US006679918B1

(12) United States Patent
Benedict et al.

(10) Patent No.: US 6,679,918 B1
(45) Date of Patent: Jan. 20, 2004

(54) IMPLANTABLE PUTTY MATERIAL (75) Inventors: James J. Benedict, Arvada, CO (US); Christopher J. Damien, Denver, CO (US)

(73) Assignee: Centerpulse Biologics Inc., Austin, TX (US)

( * ) Notice: Subject to any disclaimer, the term of this patent is extended or adjusted under 35 U.S.C. 154(b) by 0 days.

(21) Appl. No.: 09/023,617

(22) Filed: Feb. 13, 1998

Related U.S. Application Data (60) Provisional application No. 60/037,071, filed on Feb. 13, 1997.

(51) Int. Cl.[7] .................................................. C07K 1/00
(52) U.S. Cl. .......................... 623/23.61; 514/21; 514/2; 514/773; 514/801; 435/273
(58) Field of Search .............................. 514/21, 773, 2, 514/801; 435/273; 623/23.61

(56) References Cited

U.S. PATENT DOCUMENTS

| | | | | |
|---|---|---|---|---|
| 3,471,598 | A | 10/1969 | Battista | 264/28 |
| 3,949,073 | A | 4/1976 | Daniels et al. | 424/177 |
| 4,066,083 | A | 1/1978 | Ries | 128/325 |
| 4,356,572 | A | 11/1982 | Guillemin et al. | 3/1.9 |
| 4,389,487 | A | 6/1983 | Ries | 435/273 |
| 4,394,370 | A | 7/1983 | Jefferies | 424/15 |
| 4,440,750 | A | 4/1984 | Glowacki et al. | 424/95 |
| 4,563,350 | A | 1/1986 | Nathan et al. | 424/95 |
| 4,596,574 | A | 6/1986 | Urist | 623/16 |
| 4,637,931 | A | 1/1987 | Schmitz | 424/78 |
| 4,774,227 | A | 9/1988 | Piez et al. | 514/21 |
| 4,789,663 | A | 12/1988 | Wallace et al. | 514/21 |
| 4,795,467 | A | 1/1989 | Piez et al. | 623/16 |
| 4,863,732 | A | 9/1989 | Nathan et al. | 424/95 |
| 4,888,366 | A | 12/1989 | Chu et al. | 523/115 |
| 4,975,526 | A | 12/1990 | Kuberasampath et al. | 530/350 |
| 4,975,527 | A | 12/1990 | Koezuka et al. | 530/356 |
| 4,992,226 | A | 2/1991 | Piez et al. | 264/109 |
| 5,001,169 | A | 3/1991 | Nathan et al. | 523/113 |
| 5,073,373 | A | 12/1991 | O'Leary et al. | 424/422 |
| 5,236,456 | A | 8/1993 | O'Leary et al. | 623/16 |
| 5,246,457 | A | 9/1993 | Piez et al. | 623/16 |
| 5,270,300 | A | 12/1993 | Hunziker | 514/12 |
| 5,273,964 | A | 12/1993 | Lemons | 514/2 |
| 5,314,476 | A | 5/1994 | Prewett et al. | 623/16 |
| 5,332,802 | A | 7/1994 | Kelman et al. | 530/356 |
| 5,405,390 | A | 4/1995 | O'Leary et al. | 623/16 |
| 5,475,052 | A | 12/1995 | Rhee et al. | 525/54.1 |
| 6,183,737 | B1 * | 2/2001 | Zaleske et al. | |

OTHER PUBLICATIONS

Block et al., 1982, *Laboratory Medicine*, 13(5):290–298.
Guillemin et al., 1987, *J. Biomed. Mat. Res.*, 21:557–567.
Hott et al., 1991, "Ceramics in Substitutive and Reconstructive Surgery", P. Vincenzini, ed., pp. 345–352.
Sampath et al., 1987, *Proc. Natl. Acad. Sci. USA*, 84:7109–7113.

* cited by examiner

*Primary Examiner*—Leon B. Lankford, Jr.
(74) *Attorney, Agent, or Firm*—Sheridan Ross P.C.

(57) ABSTRACT

The present invention provides compositions for an implantable putty material for delivery of active compounds to a patient. More specifically, the present invention provides a material having a pH of between about 3 and 6 and possessing putty-like physical properties, wherein the composition of the material includes collagen and water. The present invention also provides a method for using the implantable putty material.

37 Claims, 5 Drawing Sheets

IMPLANTABLE PUTTY MATERIAL

CROSS REFERENCE TO RELATED APPLICATIONS

The present application claims priority under 35 U.S.C. 119 (e) to U.S. Provisional Patent Application, Ser. No. 60/037,071, filed Feb. 13, 1997, which is incorporated herein by reference.

FIELD OF THE INVENTION

The present invention relates to an implantable putty material for delivery of active compounds to a patient.

BACKGROUND OF THE INVENTION

A wide variety of implantable materials have been used in the delivery of active compounds to a patient. For example, such materials can be used in the repair of bone defects. Typically, these materials are implanted at a desired site to promote bone growth. Ideally, such a material should have the ability to adhere and conform to the implanted site and facilitate bone growth.

U.S. Pat. Nos. 5,314,476 and 5,073,373 disclose a deformable, shape-sustaining osteogenic composition comprising demineralized bone particles and a polyhydroxy compound such as glycerol, or an oligosaccharide.

U.S. Pat. Nos. 5,405,390 and 5,236,456 disclose a surface-adherent osteogenic composition derived from demineralized and thermally modified bone tissue. The composition is administered in the form of a powder, a viscous liquid, or by direct injection.

U.S. Pat. No. 5,246,457 discloses a bone-repair composition comprising a calcium phosphate salt and reconstituted fibrillar atelopeptide collagen. It does not include any biologically active ingredients. The physical and handling properties are improved by a number of curing processes, including heat, maturation of the wet mixture and/specific cross-linking of collagen.

U.S. Pat. No. 4,440,750 discloses an osteogenic composition comprising demineralized bone powder and reconstituted native atelopeptide collagen fibers in a continuous aqueous phase having a substantially physiologic pH and ionic strength.

U.S. Pat. No. 4,975,526 discloses a matrix material comprising protein-extracted demineralized bone powder and a swelling agent to increase the intraparticle porosity of the matrix.

U.S. Pat. No. 4,394,370 discloses a bone graft material for treating osseous defects. The material comprises collagen and demineralized bone particles and is sponge-like.

Currently known implantable materials, including those discussed above, are lacking in acceptable texture properties, such as cohesiveness, elasticity and the ability to be molded to a selected shape. Moreover, other paste-like materials such as those disclosed in U.S. Pat. Nos. 5,314,476 and 5,073,373 require an organic solvent such as glycerol, as discussed above.

Therefore, there is a need for an osteoinductive material which have an improved handling properties and which does not require an organic solvent.

SUMMARY OF THE INVENTION

One embodiment of the present invention is a putty material which includes collagen and water, wherein the putty material has a pH of between about 3.0 to about 6.0. Materials of the invention have excellent physical properties and handling characteristics. The collagen of the putty material can be selected from the group consisting of fibrillar collagen, atelopeptide collagen, telopeptide collagen and tropocollagen. The putty material can be formed by the addition of an acid selected from the group consisting of ascorbic acid, acetic acid, acetyl salicylic acid, benzoic acid, citric acid, glutamic acid, glycolic acid, lactic acid, malic acid, salicylic acid, and hydrochloric acid. The putty material can also include an active ingredient, such as an active ingredient selected from the group consisting of osteoinductive materials, growth factors, cartilage inducing factors, angiogenic factors, hormones, antibiotics, and antiviral compounds.

Another embodiment of the present invention is an osteogenic composition which includes collagen, an osteoinductive material, and an acid, wherein the osteogenic composition includes between about 0.05 mmol of acid per 100 mg of the collagen to about 2.3 mmol of acid per 100 mg of the collagen.

Another embodiment of the present invention is an osteogenic composition which includes bovine tendon Type I collagen, ascorbic acid, water, bone growth protein and a demineralized bone material.

Another embodiment of the present invention is a composition produced from a process including the steps of admixing collagen, an acid, and water to form a gel; and adding a demineralized bone material to said gel to produce an osteogenic putty, wherein the osteogenic putty has a pH of about 6.0 or less.

Another embodiment of the present invention is a process for making a dry osteoinductive composition comprising the steps of admixing collagen, an acid, an osteoinductive material and water to form a gel; and lyophilizing said gel.

Another embodiment of the present invention is a method for administering an active compound to a patient comprising the steps of preparing a delivery vehicle by admixing collagen and an acid to form a composition having a pH of between about 3.0 and about 6.0, incorporating an active compound into the delivery vehicle and implanting the delivery vehicle in a desired portion of the patient's body.

DETAILED DESCRIPTION OF THE INVENTION

The present invention is directed to a material composition which includes collagen and water. The material of the present invention has a putty consistency and can be molded to a desirable shape. The present invention is also directed to a process for implanting the material in the body for the purpose of stimulating or causing a biological response or activity such as inducing bone formation. Particularly, the material of the present invention is suitable for implanting in humans and animals with an osseous defect to induce the regeneration of osseous tissue to correct the defect.

The collagen component of the present invention is preferably fibrillar collagen, atelopeptide collagen, telopeptide collagen or tropocollagen and can be collected from a variety of mammalian sources. Methods for preparing atelopeptide collagen and tropocollagen are described by Glowacki et al., U.S. Pat. No. 4,440,750, which is incorporated herein in its entirety. Preferably, the collagen is a mammalian collagen. More preferably, the collagen is selected from the group consisting of bovine Type I collagen, and porcine Type I collagen, and most preferably from the group consisting of purified fibrillar bovine tendon Type I collagen. Preferably, the amount of collagen present in the materials and compositions of the present invention is from about 1% by weight (not including any water that is added) to about 10% by weight, more preferably from about 2% by weight to about 8% by weight, and most preferably from about 3% by weight to about 5% by weight.

Materials and compositions of the present invention have a pH of between about 3 and about 6, more preferably between about 3.5 and about 5, and most preferably between about 3.8 and about 4.6. The pH of the material is measured by placing a flat pH electrode on the surface of the material using Ross flat surface electrode available from Orion Co. (Boston, Mass.). It has been found that when the pH is within the limitations identified above, the materials have excellent physical properties, such as a putty consistency which is elastic and dough-like. At higher pH, the materials become crumbly with the consistency of wet sand. A putty consistency is desired because it provides many benefits such as enhanced cohesiveness, ease of handling and moldability. Because materials of the present invention are cohesive, they are also believed to provide the benefit of maintaining an active compound at the site of implantation longer than comparative materials with less cohesiveness.

A desired pH of the material of the present invention can be achieved by forming the material by adding an acid to collagen. As used in this invention, the term "acid" refers to a compound which has lower pKa than water, and the term "acidic proton" refers to a proton whose pKa is lower than water. Suitable acids for use in the present invention include organic acids, such as phenols and carboxylic acids, and inorganic acids, such as hydrochloric acid, phosphoric acid or sulfuric acid. Preferably, the acid is organic acid, hydrochloric acid, or phosphoric acid. Preferably, the acid is selected from the group consisting of acetic acid, ascorbic acid, aspartic acid, benzoic acid, citric acid, glutamic acid, glycolic acid, hydrochloric acid, lactic acid, malic acid, phosphoric acid, salicylic acid, and tartaric acid. More preferably, the acid is selected from the group consisting of ascorbic acid (i.e., vitamin C), acetic acid, acetyl salicylic acid, benzoic acid, citric acid, glutamic acid, glycolic acid, lactic acid, malic acid, salicylic acid, and hydrochloric acid. Most preferably, the acid is selected from the group consisting of ascorbic acid, citric acid, malic acid and lactic acid.

The acid should be added in a sufficient amount to produce a material with acceptable physical properties. Preferably, the amount of acid present in the material is from about 0.05 equivalent mmole (eq. mmol) of acid per 100 mg of collagen to about 2.30 eq. mmol of acid per 100 mg of collagen, more preferably from about 0.1 eq. mmol of acid per 100 mg of collagen to about 1.5 eq. mmol of acid per 100 mg of collagen, and most preferably from about 0.2 eq. mmol of acid per 100 mg of collagen to about 1.5 eq. mmol of acid per 100 mg of collagen. The term "equivalent mmole" refers to the amount of acid, in mmole, divided by the number of acidic protons present per molecule of the acid. For example, some acids such as malic acid have two equivalent acidic protons per molecule; therefore, the preferred amount of malic acid or any other acid having two acidic protons per molecule of acid is one-half that of acids having only one acidic proton. For example, 5 mmol of malic acid and 10 mmol of acetic acid can both be expressed as 10 eq. mmol of acid because malic acid has two acidic protons while acetic acid has only one acidic proton.

Another way to characterize the amount of acid present in the material is in terms of the amount of the acid per 100 mg of collagen. Thus, for example, for a material composition including ascorbic acid, it is preferred that from about 20 mg to about 200 mg of ascorbic acid is added per about 100 mg of collagen, more preferably from about 26 mg to about 131 mg of ascorbic acid per about 100 mg of collagen, and most preferably from about 65 mg to about 131 mg of ascorbic acid per about 100 mg of collagen. It should be appreciated that the amount of the acid will vary depending on its molecular weight. In the event that material is lyophilized, acid can be volatilized during lyophilization which affects the pH and the consistency of the material when the dry solid is reconstituted with water. Materials having, for example, ascorbic acid or malic acid are particularly well suited for lyophilization due to the low volatility of these acids during this process. It is preferred that the amount of acid loss during lyophilization process be less than about 30%, more preferably less than about 15%, and most preferably less than about 5%.

As discussed above, materials and compositions of the present invention have good physical properties, such as cohesiveness and retention of shape after implantation. One measure of such physical properties is that materials and compositions of the present invention have a peak resistance force of at least about 10 grams (g), preferably at least about 20 g, and more preferably at least about 30 g. As used herein, a "peak resistance force" (i.e., peak force) refers to a maximum force exerted by the material when stretched to its breaking point using a TA.XT2 Texture Analyzer apparatus which is available from Texture Technologies Corp. (Scarsdale, New York) or some equivalent apparatus. The material tested is prepared by a SMS/Kieffer molding form and press (TA-105a Texture Technologies) or some equivalent apparatus having a trapezoidal shape measuring 53 mm (1)×4 mm (h)×4 mm (w) at one end and 2.5 mm (w) at the other end.

Another measure of such physical properties is that materials and compositions of the present invention preferably have an extensibility of from about 2 mm to about 25 mm, more preferably from about 3 mm to about 25 mm, and most preferably from about 5 mm to about 25 mm. The term "extensibility" refers to the distance a probe that pulls the material travels until the material breaks when using the same apparatus and the same material dimensions for testing of peak resistance force.

Materials of the present invention can also include an effective amount of an active ingredient. An "active ingredient" refers to any compound or mixture of compounds that have a biological activity. Exemplary active ingredients include osteoinductive materials, growth factors, hormones, antibiotics, and antiviral compounds. Osteoinductive materials are described in detail below. Growth factors can include basic fibroblast growth factor (bFGF) and transforming growth factor beta (TGF-beta) (See Cuevas et al., Basic Fibroblast Growth Factor (FGF) Promotes Cartilage Repair In Vivo, Biochem Biophys Res Commun 156:611–618, 1988). These growth factors have been implicated as cartilage stimulating and angiogenic agents. bFGF, for example, has been shown to increase the rate of osteoblast replication while simultaneously inhibiting their activity (Frenkel S, Singh IJ; The effects of fibroblast growth factor on osteogenesis in the chick embryo. In: Fundamentals of bone growth: Methodology and applications. Ed. AD Dixon, BG Sarnat, D. Hoyte, CRC Press, Boca Raton, Fl., USA, pp. 245–259, 1990). This effect is dose dependent, with higher and lower doses causing decreased activity and middle range doses stimulating activity (Aspenberg P, Thorngren KG, Lohmander LS; Dose-dependent stimulation of bone induction by basic fibroblast growth factor in rats. Acta Orthop Scand 62:481–484, 1991).

The term "effective amount" refers to an amount of an active ingredient sufficient to achieve a desired affect without causing an undesirable side effect. In some cases, it may be necessary to achieve a balance between obtaining a desired effect and limiting the severity of an undesired effect. It will be appreciated that the amount of active ingredient used will vary depending upon the type of active ingredient and the intended use of the composition of the present invention. When the material of the present invention includes an osteogenic material, the amount of osteoinductive material is preferably between about 0.1% by weight and about 10% by weight of the total weight of the putty material, more preferably between about 0.25% by weight and about 4% by weight, and most preferably between about 0.35% by weight and about 1.6% by weight.

An "osteoinductive material" refers to any material that is capable of inducing bone formation (i.e., a material having osteogenic properties) when implanted in a body and includes demineralized bone matrix and osteoinductive factors. An "osteoinductive factor" refers to a natural, recombinant or synthetic protein or mixture of proteins which are capable of inducing bone formation. For example, the term osteoinductive factor refers to the materials described as bone growth factors in Damien et al., U.S. Pat. No. 5,563,124. It should be noted that while most contemplated applications of the present invention are concerned with use in humans, the products and processes of the present invention work in animals as well. Induction of bone formation can be determined by a histological evaluation showing the de novo formation of bone with accompanying osteoblasts, osteoclasts, and osteoid matrix. For example, osteoinductive activity of an osteoinductive factor can be demonstrated by a test using a substrate onto which material to be tested is deposited. A substrate with deposited material is implanted subcutaneously in a test animal. The implant is subsequently removed and examined microscopically for the presence of bone formation including the presence of osteoblasts, osteoclasts, and osteoid matrix. A suitable procedure is illustrated in Example 5 of U.S. Pat. No. 5,290,763.

No generally accepted scale for evaluating the degree of osteogenic activity exists, however, certain factors are widely recognized as indicating bone formation. Such factors are referenced in the scale of 0–8 which is provided in Table 3 of Example 1 of U.S. Pat. No. 5,563,124. The 0–4 portion of this scale corresponds to the scoring system described in U.S. Pat. No. 5,290,763, which is limited to scores of 0–4. The remaining portion of the scale, scores 5–8, references additional levels of maturation of bone formation. The expanded scale also includes consideration of resorption of collagen, a factor which is not described in U.S. Pat. No. 5,290,763.

Suitable osteoinductive factors of the present invention can be produced by purification of naturally occurring proteins from bone or by recombinant DNA techniques. As used herein, the term recombinantly produced osteoinductive factors refers to the production of osteoinductive factors using recombinant DNA technology. For example, nucleic acids encoding proteins having osteogenic activity can be identified by producing antibodies that bind to the proteins. The antibodies can be used to isolate, by affinity chromatography, purified populations of a particular osteogenic protein. The amino acid sequence can be identified by sequencing the purified protein. It is possible to synthesize DNA oligonucleotides from the known amino acid sequence. The oligonucleotides can be used to screen either a genomic DNA and/or cDNA library made from, for example bovine DNA, to identify nucleic acids encoding the osteogenic protein. The correct oligonucleotide will hybridize to the appropriate cDNA thereby identifying the cDNA encoding the osteogenic protein encoding gene.

Antibodies that bind osteogenic proteins can also be used directly to screen a cDNA expression library. For example, eukaryotic cDNA sequences encoding osteogenic proteins can be ligated into bacterial expression vectors. The expression vectors can be transformed into bacteria, such as *E. coli*, which express the transformed expression vector and produce the osteogenic protein. The transformed bacteria can be screened for expression of the osteogenic protein by lysing the bacteria and contacting the bacteria with radioactively-labelled antibody.

Recombinant osteoinductive factor can be produced by transfecting genes identified according to the method described above into cells using any process by which nucleic acids are inserted into cells. After transfection, the cell can produce recombinant osteoinductive factors by expression of the transfected nucleic acids and such osteoinductive factors can be recovered from the cells.

A number of naturally occurring proteins from bone or recombinant osteoinductive factors have been described in the literature and are suitable for the present invention. Recombinantly produced osteoinductive factors have been produced by several entities. Creative Biomolecules of Hopkinton, Mass., USA produces a osteoinductive factor referred to as Osteogenic Protein 1 or OP1. Genetics Institute of Cambridge, Mass., USA produces a series of osteoinductive factors referred to as Bone Morphogenetic Proteins 1–13 (i.e., BMP 1–13), some of which are described in U.S. Pat. Nos. 5,106,748 and 5,658,882 and in PCT Publication No. WO 96/39,170. Purified osteoinductive factors have been developed by several entities. Collagen Corporation of Palo Alto, Calif., USA developed a purified protein mixture which is believed to have osteogenic activity and which is described in U.S. Pat. Nos. 4,774,228; 4,774,322; 4,810,691; and 4,843,063. Marshall Urist of the University of California developed a purified protein mixture which is believed to be osteogenic and which is described in U.S. Pat. Nos. 4,455,256; 4,619,989; 4,761,471; 4,789,732; and 4,795,804. International Genetic Engineering, Inc. of Santa Monica, Calif., USA developed a purified protein mixture which is believed to be osteogenic and which is described in U.S. Pat. No. 4,804,744. All of the foregoing patents are incorporated herein by reference.

Figure 1:
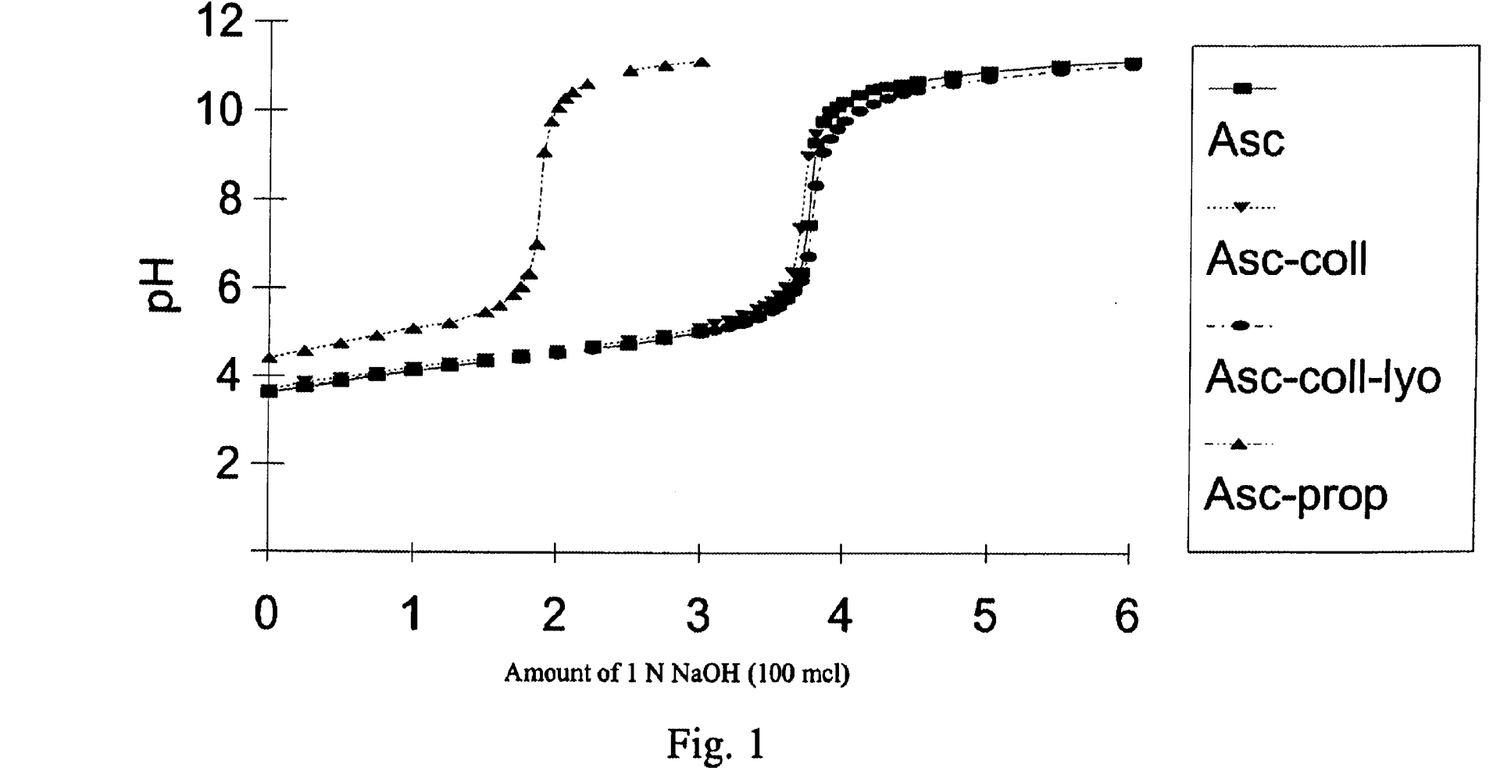
FIG. 1 illustrates volatility of ascorbic acid from an implantable material during lyophilization process.
Figure 2:
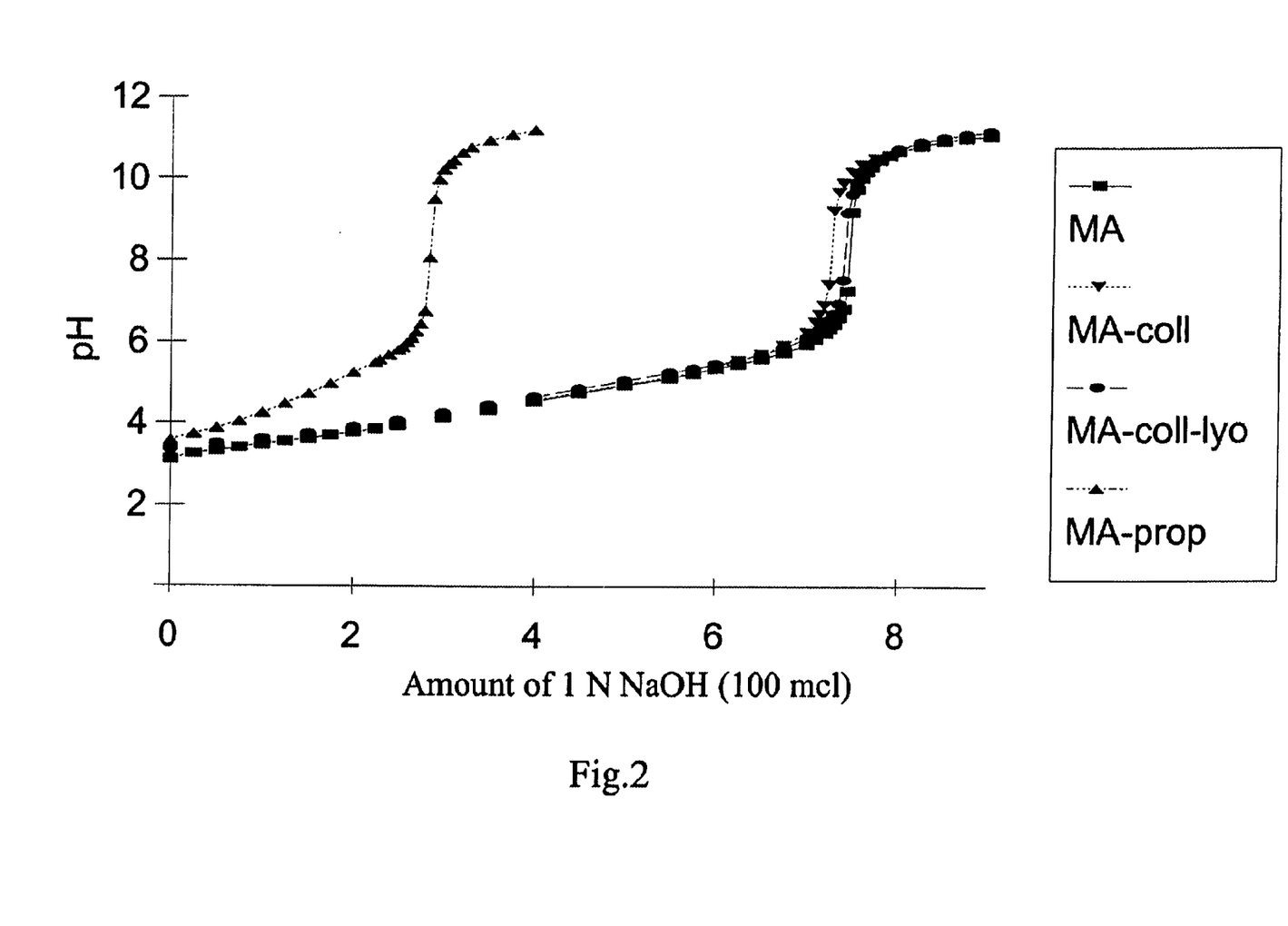
FIG. 2 illustrates volatility of malic acid from an implantable material during lyophilization process.
Figure 3:
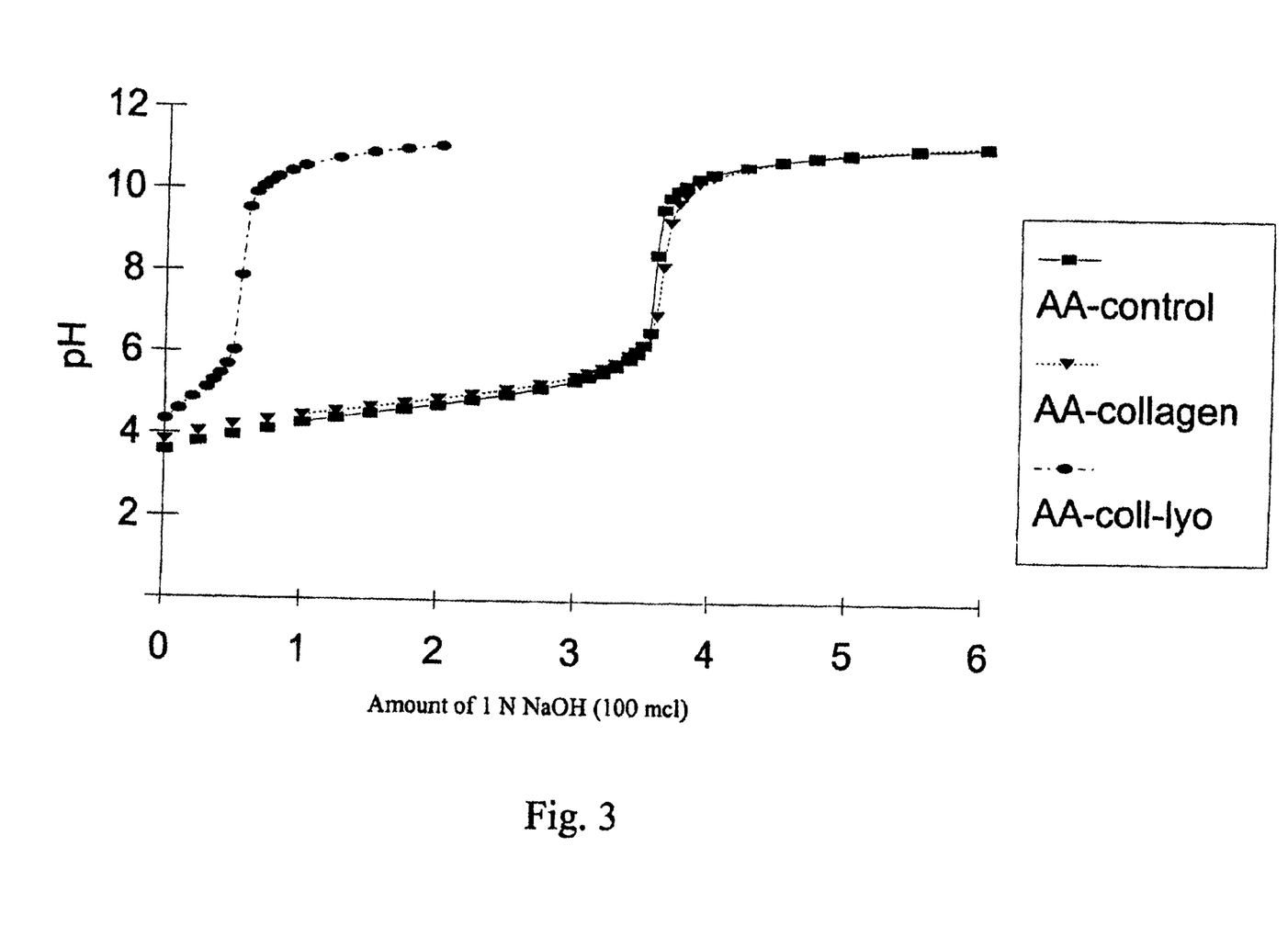
FIG. 3 illustrates volatility of acetic acid from an implantable material during lyophilization process.
Figure 4:
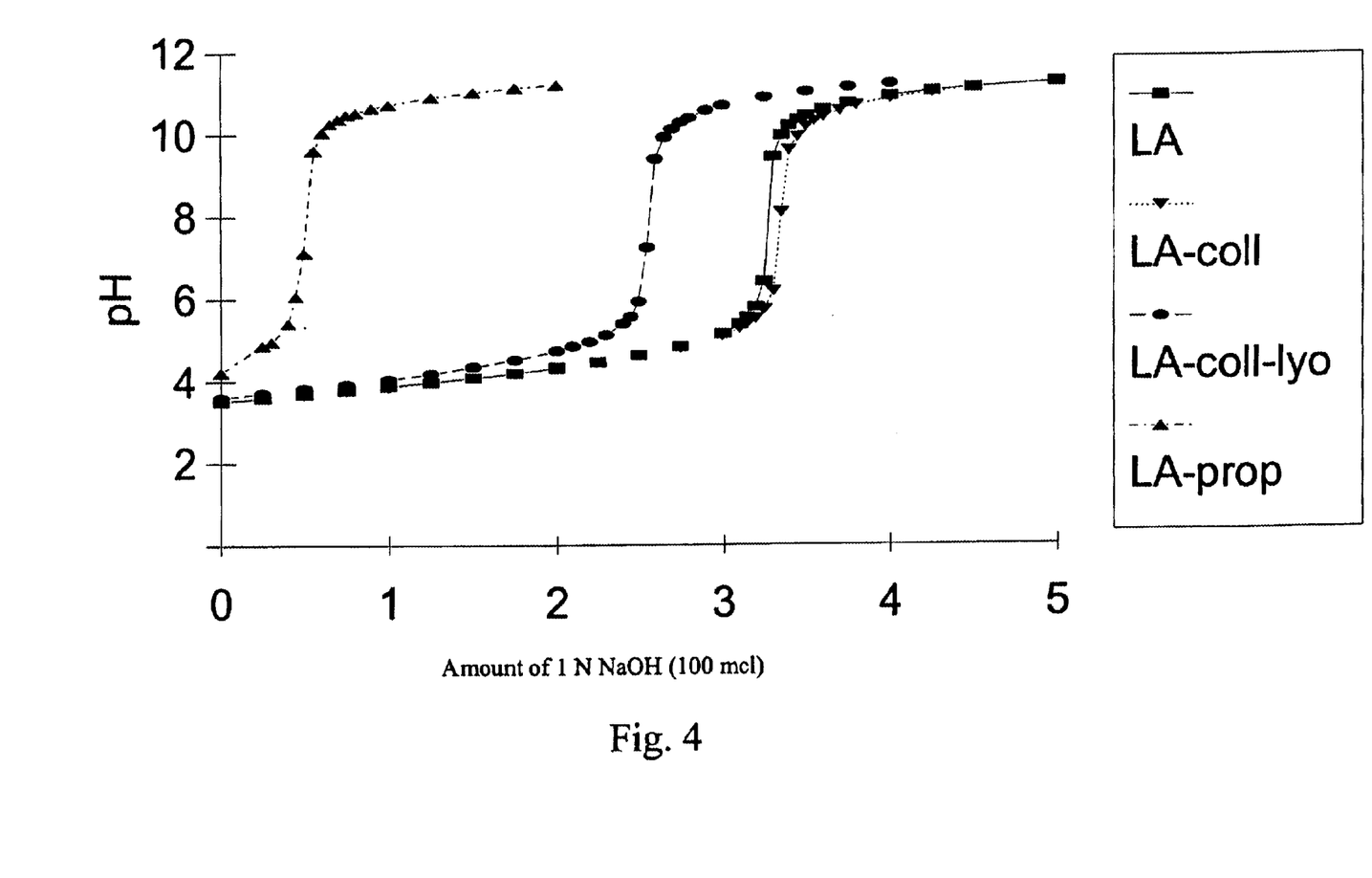
FIG. 4 illustrates volatility of lactic acid from an implantable material during lyophilization process.
Figure 5:
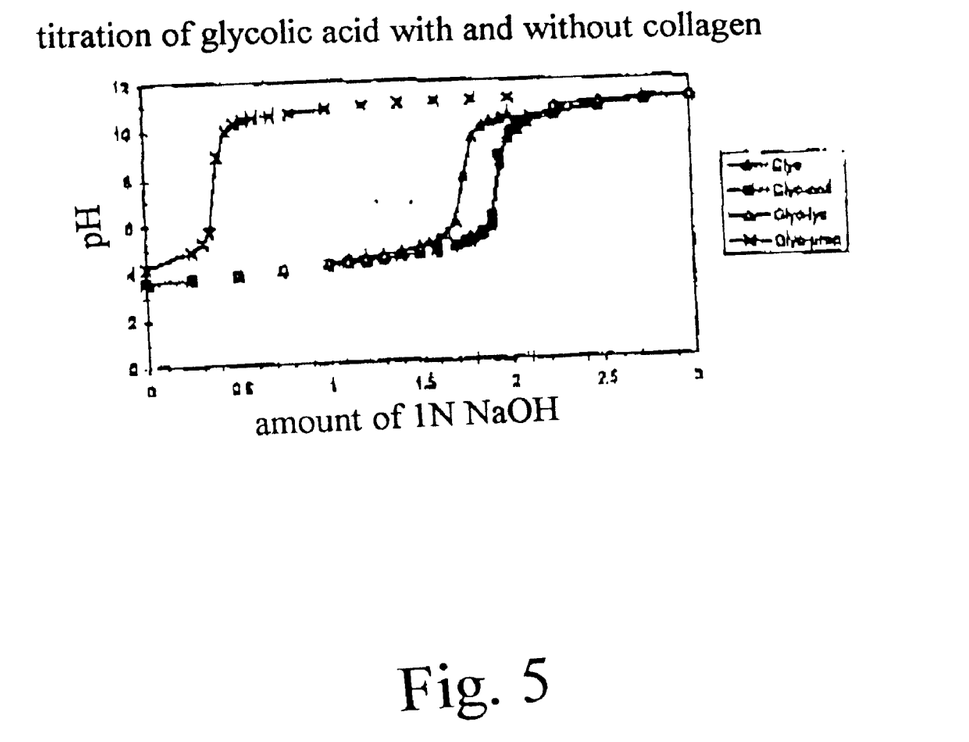
FIG. 5 illustrates volatility of glycolic acid from an implantable material during lyophilization process.

A preferred osteoinductive factor of the present invention and process for making the same is described in detail in related U.S. Pat. No. 5,290,763. This osteoinductive factor is particularly preferred because of its high osteogenic activity and because it is a purified osteoinductive factor. The osteoinductive factor of U.S. Pat. No. 5,290,763 exhibits osteoinductive activity at about 3 micrograms when deposited onto a suitable carrier and implanted subcutaneously into a rat. In one embodiment, the osteoinductive factor is an osteoinductively active mixture of proteins which exhibit the gel separation profile shown in FIG. 1 of U.S. Pat. No. 5,563,124. This gel separation profile was obtained using SDS-PAGE. The first column is a molecular weight scale which was obtained by performing SDS-PAGE on standards of known molecular weight. The second column illustrates the SDS-PAGE profile for a mixture of proteins in accordance with the present invention which have been reduced with 2-mercaptoethanol. The third column illustrates the SDS-PAGE profile for a non-reduced mixture of proteins in accordance with the present invention. Although the mixture of proteins which provide the SDS-PAGE profile illustrated therein have been found to have high osteoinductive activity, it is anticipated that mixtures of proteins having SDS-PAGE profiles which differ slightly from that illustrated therein will also be effective. For example, effective protein mixtures can include proteins that differ in molecular weight by plus or minus 5 KD from those shown therein, and can include fewer or greater numbers of proteins than those shown. Therefore, mixtures of proteins having profiles which comprise substantially all of the protein bands detected in the reduced or nonreduced SDS-PAGE profiles therein will be considered to be within the scope of the invention.

Yet another embodiment of the preferred osteoinductive factor of the invention includes an osteoinductively active mixture of proteins having, upon hydrolysis, an amino acid composition of from about 20.7 to about 26.1 mole percent acidic amino acids, about 11.3 to about 15.7 mole percent hydroxy amino acids, about 37.6 to about 42.4 mole percent aliphatic amino acids, about 5.8 to about 7.9 mole percent aromatic amino acids and about 13.3 to about 19.9 mole percent basic amino acids. More particularly, the preferred osteoinductive factor has an amino acid composition of about 20.7 to about 26.1 (preferably about 23.4) mole percent of ASP (+ASN) and GLU(+GLN); about 11.3 to about 15.7 (preferably about 13.5) mole percent SER and THR; about 37.6 to about 42.4 (preferably about 40.0) mole percent ALA, GLY, PRO, VAL, MET, ILE, and LEU; about 5.8 to about 7.9 (preferably about 6.8) mole percent TYR and PHE; and about 13.3 to about 19.9 (preferably about 16.6) mole percent HIS, ARG, and LYS. A further embodiment of the preferred osteoinductive factor is a protein mixture having the approximate amino acid composition shown in Table 1.

TABLE 1

| Amino Acid | Mole Percent |
| --- | --- |
| Asp | 11.14 |
| Glu | 12.25 |
| Ser | 9.48 |
| Gly | 8.50 |
| His | 2.28 |
| Arg | 7.19 |
| Thr | 4.03 |
| Ala | 8.05 |
| Pro | 7.16 |
| Tyr | 3.63 |
| Val | 3.79 |
| Met | 1.73 |
| Ile | 2.75 |
| Leu | 8.00 |
| Phe | 3.21 |
| Lys | 7.11 |

A still further embodiment of the preferred osteoinductive factor is a protein mixture obtained by any of the purification processes described in U.S. Pat. No. 5,290,763.

Materials of the present invention are typically derived by admixing collagen, water and an acid. As discussed above, the material can also include other substances such as an active ingredient. The material can also be sterilized by dialysis, irradiation (e.g. using g-radiation), filtration, chemical treatment (e.g., using ethylene oxide), or other known sterilization methods. Alternatively, the material which can be a gel is lyophilized to a dry solid before being sterilized. When sterilizing the material using a chemical treatment, it is preferred that the material be lyophilized to a dry solid prior to being sterilized. Lyophilization removes water and prevents any chemical reaction which may occur between the chemical used for sterilization (e.g., ethylene oxide) and water. Another alternative method is to make the material of the present invention in an aseptic environment, thereby eliminating the need for a separate sterilization step.

Materials of the present invention can also include demineralized bone material. A method for preparing demineralized bone material in a particulate form is described by Glowacki et al., U.S. Pat. No. 4,440,750. Alternatively demineralized bone material can be prepared by grinding a bone, demineralizing it with 0.6 M HCl solution, washing with a phosphate buffered solution, washing with ethanol and drying it. Demineralized bone material can also be obtained from a commercial bone or tissue bank, for example, from AlloSource (Denver, Colo.).

Materials of the present invention can be part of a kit containing the components of the materials. Such kits are particularly useful for health care professionals in preparing the materials and compositions of the present invention immediately before use. Such kits, in addition to including the component parts of the various materials and compositions of the invention also include one or more containers for mixing the components, along with optional mixing devices such as stirrers. Further, such kits can include the components in sealed, pre-measured packages. The sealed packages can be sealed aseptically and the amounts of the components can be pre-measured in relative amounts as described elsewhere herein.

Another aspect of the present invention includes a process of implanting a material or composition as broadly described above into a body. As noted above, most uses of the present invention are concerned with human application. The process, however, is applicable to a wide variety of animals, particularly mammals. As used in this invention, the term "implanting" refers to placing the material or composition of the present invention in an area in which it is desired to achieve the activity of the active ingredient. In this embodiment of the present invention, the materials function as a delivery vehicle for an active ingredient. Such methods of implantation can involve a surgery or a simple injection of the product using any of the known methods including a use of syringe.

For the product of the present invention comprising an osteogenic composition, the present material and process can be used in a variety of application whenever there is a need to generate bone. Such applications include induction of bone formation for hip replacement operations, knee replacement operations, spinal fusion procedures, repair of periodontal defects, treatment of osteoporosis, repair of bone tumor defects, dental procedures, repair of cranialmaxillafacial defects, and repair of bone fractures.

In the case of hip replacement operations, the ball and socket joint of a hip is replaced when a person's hip is not functioning properly. The ball portion of a joint is replaced by surgical removal of the ball portion from the terminus of the femur. The artificial ball portion has a functional ball end with the opposite end being a spike which is inserted into the proximal end of the femur from which the natural ball portion was removed. The spike can have a porous surface so that bone growth around the spike can anchor the spike in the femur. Materials of the present invention can be layered or packed between the spike and the cavity in the femur in which spike is to be inserted. The socket portion of a joint is replaced by inserting an artificial socket into the natural socket. The artificial socket is sized to fit with the artificial ball. On the surface of the artificial socket which contacts the natural socket, the artificial socket can have a porous surface. Materials of the present invention can be placed in the natural socket cavity so that upon placement of the artificial socket, the material is between the natural and artificial socket. In this manner, as bone is formed, the artificial socket is anchored in the natural socket.

Materials of the present invention are also suitable for use in knee replacement operations. Knee prostheses have a femoral and a tibial component which are inserted into the distal end of the femur and the surgically prepared end of the tibia, respectively. Materials of the present invention can be layered or packed between the femoral and/or tibial components of the prosthesis and the respective portions of the femur and tibia. In this manner, as bone formation is induced between the prosthesis and the bones, the prosthesis becomes anchored.

Materials of the present invention are also suitable for use in spinal fusion operations in which it is desired to substantially immobilize two vertebrae with respect to each other. The material can be applied, for example, between adjacent spinous and transverse processes so that upon bone formation throughout the material, two adjacent vertebrae are joined by fusion between the respective spinous processes and transverse processes.

Materials of the present invention can also be used in spinal fusion operations in which it is desired to substantially immobilize two vertebrae with respect to each other by using metal cages or equivalent implants. In this case, the cages are placed in the disk space between two vertebral bodies, and the material of the present invention is packed into and around the cages to obtain bone formation through and around the cages thus fusing two vertebrae and stabilizing the spine.

EXAMPLES

Unless otherwise stated, following general procedures were used throughout the Examples.

Bovine demineralized bone material was prepared by grinding bovine bone to a particle size of about 125 μm to about 850 μm. It was demineralized in 0.6 M HCl, washed with phosphate buffered solution, rinsed with ethanol and dried.

The putty materials were tested using TA-XT2 Texture Analyzer having following testing parameters: pre-test speed=2.0 mm/sec, test speed=3.3 mm/sec, post test speed= 10.0 mm/s, distance=30 mm, trigger force=3 g.

The pH of putty materials were measured using Ross flat surface electrode available from Orion Co. (Boston, Mass.).

Example 1

This example illustrates the effect of acid on the consistency of the material produced when combined with collagen and demineralized bone material.

For each acid and molarity concentration tested, a gel was prepared by mixing 100 mg of purified bovine tendon Type I collagen and 7.4 mL of aqueous acid solution. The gel was lyophilized and then mixed with water and about 2.1 g to about 2.4 g of demineralized bone material. The resulting composition was qualitatively evaluated for its physical properties by manual examination for properties such as cohesiveness, elasticity and moldability. Each gel was graded as having acceptable physical properties or not. Some acids, such as ascorbic acid and benzoic acid, showed a wide range of useful concentrations in producing a composition having acceptable physical properties, while others such as acetic acid and lactic acid showed a narrow range of amount which is suitable for producing a composition with putty consistency. If a gel was found to initially have acceptable physical properties, it was then subjected to ethylene oxide sterilization and re-evaluated. Table 2 summarizes the qualitative evaluation of the compositions tested.

TABLE 2

| Acid | nM (mequiv.) | Avg. pH (w/DBM) | Acceptable Physical Properties | Post ethylene oxide Acceptable Physical Properties |
|---|---|---|---|---|
| Acetic Acid | 6.67 (0.007) | 5.95 | N | N/A |
| " | 33.3 (0.037) | 4.97 | N | N/A |
| " | 50.0 (0.056) | N/R | N | N/A |
| " | 66.6 (0.074) | 4.85 | N | N/A |
| " | 100 (0.111) | N/R | Y | N |
| " | 167 (0.185) | 4.51 | Y | N |
| " | 333 (0.370) | 4.09 | Y | N/A |
| Ascorbic Acid | 10 (0.074) | N/R | N | N |
| " | 20 (0.148) | N/R | Y/N | N |
| " | 30 (0.222) | 4.33 | Y | Y |
| " | 50 (0.370) | 4.10 | Y | Y |
| " | 100 (0.740) | N/R | Y | Y |
| " | 50 (0.370) | 4.46 | Y | N/A |
| " | 50 (0.370) | 4.64 | N | N/A |
| " | 50 (0.370) | N/R | N | N/A |
| " | 50 (0.370) | N/R | N | N/A |
| " | 30 (0.444) | N/R | N | N/A |
| Benzoic Acid | 10 (0.074) | N/R | N | N |
| " | 25 (0.185) | N/R | Y | N |
| Citric Acid | 10 (0.148) | N/R | N | |
| " | 20 (0.298) | N/R | N | N/A |
| " | 50 (0.740) | N/R | Y | N |
| " | 100 (1.480) | 3.58 | Y | N |
| " | 100 (1.480) | 3.77 | Y | N/A |
| " | 100 (1.480) | 3.95 | Y/N | N/A |
| " | 100 (1.480) | 4.05 | N | N/A |
| Glutamic Acid | 10 (0.148) | N/R | N | N/A |
| " | 100 (1.480) | N/R | N | N/A |
| Glycolic Acid | 100 (0.659) | N/R | Y | N |
| Hydrochloric Acid | 10 (0.074) | 5.76 | Y/N | N |
| Hydrochloric Acid | 100 (0.740) | N/R | N | N/A |
| Lactic Acid | 1.9 (0.010) | 6.50 | N | N/A |
| " | 9.4 (0.051) | 6.17 | N | N/A |
| " | 10 (0.054) | N/R | N | N/A |
| " | 24 (0.130) | 5.18 | Y/N | N/A |
| " | 30 (0.162) | 4.09 | Y | N/A |
| " | 47 (0.254) | 4.48 | Y | N/A |
| " | 60 (0.324) | 3.94 | Y | N |
| " | 100 (0.540) | N/R | N | N/A |
| " | 100 (0.540) | 4.38 | N | N/A |
| " | 100 (0.540) | 4.55 | N | N/A |
| " | 100 (0.540) | 4.85 | N | N/A |
| " | 100 (0.540) | 5.17 | N | N/A |
| " | 100 (0.540) | 5.56 | N | N/A |
| " | 188 (1.016) | 3.75 | Y/N | N/A |
| Malic Acid | 10 (0.148) | N/R | N | N/A |
| " | 30 (0.444) | 4.00 | Y | N/A |
| " | 50 (0.740) | 3.77 | Y | N |
| " | 100 (1.48) | N/R | Y | N/A |
| Phosphoric Acid | 5.4 (0.80) | 6.11 | N | N/A |
| " | 10.8 (0.160) | 5.91 | N | N/A |
| " | 50 (0.740) | N/R | Y | N/A |
| " | 100 (1.480) | N/R | N | N/A |
| Salicylic Acid | 10 (0.074) | N/R | Y | N |
| Tartaric Acid | 100 (1.480) | N/R | Y | N/A |

N/R = not recorded, N/A = not applicable (not tested) and Y/N = marginally acceptable results.

Example 2

This example illustrates the amount of acid loss during lyophilization of compositions and the physical properties of the resulting material before and after ethylene oxide sterilization.

A control solution of 500 μL of a 1 M solution of the acids tested in 100 mL of water was titrated with 1 N NaOH solution. To test for the amount of acid loss during lyophilization, samples were prepared using the procedure of Example 1, except that no demineralized bone material was added after lyophilization. The resulting material was dissolved in water (at a ratio of 1 g of lyophilized material/100 mL), and titrated with 1 N NaOH solution. The materials, except the one made with acetic acid were subsequently treated with 2-propanol and titrated as follows. The lyophilized samples of collagen/acid mixture were chopped in 2-propanol and relyophilized to free much of the acid which was then removed by the second lyophilization as evidenced when the samples were titrated after this treatment. The results of titrations curves for materials made with ascorbic acid, malic acid, acetic acid, lactic acid and glycolic acid are shown in FIGS. 1–5, respectively. The amount of acid loss and the amount of acid remaining in the samples are shown on Table 3.

TABLE 3

| Acid | mM | % Acid loss | mg Acid in sample | wt % of acid in sample |
|---|---|---|---|---|
| Acetic Acid | 50 | 85 | 3.33 | 3.2 |
| Ascorbic Acid | 10 | 0 | 13.03 | 11.5 |
| " | 20 | 0 | 26.07 | 20.7 |
| " | 50 | 0 | 65.17 | 39.5 |
| " | 100 | 0 | 130.34 | 56.6 |
| Citric Acid | 10 | 0 | 14.22 | 12.4 |
| " | 20 | 0 | 28.43 | 22.1 |
| " | 50 | 0 | 71.08 | 41.5 |
| " | 100 | 0 | 142.17 | 58.7 |
| Hydrochloric Acid | 10 | 7 | 2.70 | 2.6 |
| Lactic Acid | 50 | 27 | 24.33 | 19.6 |
| " | 100 | 27 | 48.66 | 32.7 |
| Glycolic Acid | 50 | 11 | 28.14 | 22.0 |
| " | 100 | 11 | 56.28 | 36.0 |
| Malic Acid | 50 | 0 | 49.61 | 33.2 |
| " | 100 | 0 | 99.23 | 49.8 |

These results indicate that ascorbic acid, citric acid and malic acid were of relatively low volatility and acetic acid was found to be the most volatile.

Example 3

This example illustrates bioactivity of the implantable materials having various acids.

A gel was prepared by mixing 100 mg of collagen, 7.4 mL of aqueous acid solution of a given molarity, and a given amount of bone growth protein (BGP) as described in U.S. Pat. No. 5,290,763. The gel was lyophilized and some of the lyophilized gels were sterilized by contacting with ethylene oxide. About 15 mg of lyophilized gel is mixed with 1.14 mL of water and 173 mg of rat demineralized bone material. The resulting material was placed in a mold and 12 to 15 disks of 7 mm diameter and 2 mm thickness was formed. The disks were frozen, lyophilized overnight, and implanted subcutaneously in rats. The animals were sacrificed after 28 days and histological slides were made of the explanted tissues. Acid fuchsin and Sanderson's Rapid Bone Stain or toluidine blue were used to stain the explanted tissue slides to facilitate viewing of bone and cartilage formation. The type and molarity of each acid tested, the amount of BGP added, and whether the gel was exposed to ethylene oxide are set forth in Table 4.

TABLE 4

| Acid | mM | BGP (μg) | Ethylene oxide exposure? |
|---|---|---|---|
| H₂O (control) | — | 20 | Y |
| Ascorbic Acid | 10 | 20 | Y |
| " | 20 | 20 | Y |
| " | 30 | 20 | Y |
| " | 50 | 0 | N |
| " | 50 | 10 | N |
| " | 50 | 20 | Y |
| " | 50 | 3.5 | N |
| " | 50 | 35 | N |
| " | 50 | 8 | N |
| " | 100 | 20 | Y |
| Benzoic Acid | 25 | 20 | Y |
| Citric Acid | 50 | 20 | Y |
| Glycolic Acid | 50 | 10 | N |
| " | 50 | 20 | Y |
| Lactic Acid | 50 | 20 | Y |
| " | 100 | 10 | N |
| Malic Acid | 50 | 10 | N |
| " | 50 | 20 | Y |

Materials made with lactic acid at 50 mM and 100 mM, and ascorbic acid at 10 mM, 20 mM, 30 mM, 50 mM and 100 mM showed good complete ossicle formation. Bone was seen throughout the explanted tissue. There was generally a mature rim of bone and an occasional pocket of soft tissue. Results of materials made with malic acid at 50 mM, glycolic acid at 50 mM, citric acid at 50 mM and benzoic acid at 25 mM varied from sparse islands to full ossicles. The sensitivity of the osseoinductive response to BGP does was evaluated with ascorbic acid at 50 mM. The results showed no bone formation at 0 BGP, and at 35 μg, significantly larger amounts of bone growth occurred. The results also indicate that, after ethylene oxide exposure, the osseoinductive response appears to be inversely related to the molarity of the acid. Good bone formation was observed where ascorbic acid at 30 mM and 50 mM was added to a mixture of collagen and BGP that had not been exposed to ethylene oxide, even where the ascorbic acid had itself been exposed separately to ethylene oxide. Good bone formation was observed in samples made using 10 mM and 20 mM ascorbic acid, regardless of whether it was exposed to ethylene oxide or not.

Example 4

This example illustrates the effect of adding an acidic buffer solution to a lyophilized collagen material just prior to addition of the demineralized bone matrix.

Instead of preparing the collagen with the acid solution and then lyophilizing the material as described in Experiment 1, a sample of collagen was prepared with a dilute, volatile acid (e.g., acetic acid) and lyophilized. This material when reconstituted with water resulted in subjectively poor handling properties and could not be tested objectively using the methods described in the following examples. When the same material was reconstituted by adding an acid buffer solution instead of water, the resulting material was in a putty form that was both subjectively adequate and was testable using the experimental procedures described in the following examples. A variety of acid buffer solutions, including ascorbic acid at 20, 30, 50 and 100 mM, citric acid at 50 mM, malic acid at 50 mM, and lactic acid at 50 mM, can be used as an acid buffer solution in reconstituting the lyophilized collagen to obtain a material having a desired physical properties.

Example 5

This example illustrates effect of different acids in extensibility and peak resistance force (peak force) of a material.

Gels were prepared and lyophilized using the procedure of Example 4. Lyophilized gels were refrigerated until use.

Samples for physical property testing were prepared by adding 6 mL of water to the lyophilized gel. About 1.75 g of bovine demineralized bone material having a particle size of from 125 μm to about 850 μm was added, mixed and allowed to stand for about 5 minutes, unless otherwise noted. The putty was then placed in an SMS/Kieffer molding form and press (TA-105a Texture Technologies). This produced test specimens having a trapezoidal shape measuring 53 mm (l)×4 mm (h)×4 mm (w) at one end and 2.5 mm (w) at the other end. Table 5 shows a peak force and a distance to peak force measured using TA-XT2 texture analyzer with test rate (i.e., rate of probe travel) of 2.0 mm/sec and trigger force of 5.0 g for putty materials having a various acid solutions.

TABLE 5

| Acid | Distance (mm) | Peak Force (g) |
| --- | --- | --- |
| 50 mM Ascorbic Acid | −6.75 ± 0.48 | 58.21 ± 5.11 |
| 50 mM Acetic Acid | −0.93 ± 0.07 | 6.65 ± 0.23 |
| 50 mM Citric Acid | −10.83 ± 0.67 | 39.72 ± 5.41 |
| 10 mM HCl | −4.25 ± 0.16 | 20.24 ± 2.54 |
| 50 mM Lactic Acid | −7.50 ± 0.35 | 49.28 ± 4.45 |

Without being bound by a theory, the poor result of 50 mM acetic acid sample is believed to be due to the volatility of acetic acid during lyophilization process where about 85% of the acetic acid is lost.

Example 6

This example illustrates the effect of different acid concentration on the physical property of a putty material.

Samples using solution of a various concentrations of ascorbic acid and citric acid were prepared and tested using the procedure of Example 6. The results are shown in Table 5. In general, as the concentration of acid increases the extensibility of the putty material increases.

TABLE 6

| Acid | pH | Distance (mm) | Peak Force (g) |
| --- | --- | --- | --- |
| 10 mM Ascorbic Acid | 5.7 | −1.74 ± 0.49 | 38.84 ± 20.69 |
| 20 mM Ascorbic Acid | 5.0 | −3.58 ± 0.18 | 80.31 ± 24.65 |
| 50 mM Ascorbic Acid | 4.6 | −6.21 ± 0.34 | 47.55 ± 12.09 |
| 100 mM Ascorbic Acid | 4.1 | −6.96 ± 0.81 | 40.28 ± 8.82 |
| 10 mM Citric Acid | 5.0 | −3.25 ± 1.37 | 26.39 ± 11.15 |
| 20 mM Citric Acid | 4.6 | −4.76 ± 0.46 | 71.49 ± 15.98 |
| 50 mM Citric Acid | 4.1 | −11.74 ± 0.89 | 88.71 ± 11.19 |
| 100 mM Citric Acid | 3.3 | −11.55 ± 0.76 | 42.41 ± 3.36 |

Example 7

This example illustrates the effect of preparation time on the pH, distance to peak force and peak force of a putty material.

Samples using 50 mM ascorbic acid, 50 mM citric acid and 100 mM citric acid solutions were prepared and tested using the procedure of Example 5. Stand times for the putty materials were varied at 2, 5, 10 and 20 minutes. The results are shown on Table 7.

TABLE 7

| Acid | time (min) | Distance (mm) | Peak Force (g) |
| --- | --- | --- | --- |
| 50 mM Ascorbic Acid | 2 | −11.75 ± 0.43 | 54.51 ± 4.82 |
| 50 mM Ascorbic Acid | 5 | −12.87 ± 2.30 | 56.90 ± 6.25 |
| 50 mM Ascorbic Acid | 10 | −10.53 ± 0.52 | 74.21 ± 7.24 |
| 50 mM Ascorbic Acid | 20 | −8.40 ± 0.80 | 58.11 ± 7.82 |
| 50 mM Citric Acid | 2 | −17.56 ± 1.82 | 35.30 ± 2.34 |
| 50 mM Citric Acid | 5 | −18.56 ± 3.17 | 49.49 ± 5.12 |
| 50 mM Citric Acid | 10 | −16.66 ± 1.50 | 54.74 ± 6.42 |
| 50 mM Citric Acid | 20 | −18.32 ± 1.24 | 55.13 ± 8.53 |
| 100 mM Citric Acid | 2 | −11.32 ± 0.62 | 21.61 ± 4.13 |
| 100 mM Citric Acid | 5 | −10.54 ± 0.32 | 19.32 ± 1.58 |
| 100 mM Citric Acid | 10 | −10.79 ± 0.66 | 25.87 ± 3.90 |
| 100 mM Citric Acid | 20 | −14.42 ± 1.10 | 31.84 ± 4.26 |

Distance to peak force are similar for putty materials having a stand time of 2, 5 and 10 minutes. More importantly, the pH of the putty materials changed slightly with time as shown on Table 8.

TABLE 8

| pH of Putty Materials over Time | | | | |
| --- | --- | --- | --- | --- |
| Acid (amount of acid) | 2 min | 5 min | 10 min | 20 min |
| 50 mM Ascorbic Acid (65.2 mg) | 4.4 | 4.3 | 4.5 | 4.6 |
| 50 mM Citric Acid (71.1 mg) | 3.8 | 3.9 | 4.0 | 4.0 |
| 100 mM Citric Acid (142.2 mg) | 3.4 | 3.3 | 3.4 | 3.5 |

Example 8

This example illustrates the effect of ethylene oxide sterilization on the physical properties of putty materials.

Samples using 20 mM and 50 mM ascorbic acid, and 50 mM and 100 mM citric acid solutions were prepared using the procedure of Example 5 and sterilized with ethylene oxide by MMC (Erie, Pa.). A comparative distance to peak force and peak force are shown on Table 9.

TABLE 9

| Effect of Ethylene Oxide Sterilization | | | | |
| --- | --- | --- | --- | --- |
| Acid | Sterilized? | pH | Distance (mm) | Peak Force (g) |
| 20 mM Ascorbic Acid | Y | 5.0 | −4.30 ± 0.34 | 8.22 ± 1.53 |
| 20 mM Ascorbic Acid | N | 4.9 | −5.11 ± 1.26 | 13.57 ± 4.13 |

TABLE 9-continued

Effect of Ethylene Oxide Sterilization

| Acid | Sterilized? | pH | Distance (mm) | Peak Force (g) |
|---|---|---|---|---|
| 50 mM Ascorbic Acid | Y | 4.4 | −9.30 ± 1.13 | 18.49 ± 1.68 |
| 50 mM Ascorbic Acid | N | 4.3 | −12.54 ± 1.32 | 56.17 ± 7.91 |
| 50 mM Citric Acid | Y | 4.1 | 0 | <3 |
| 50 mM Citric Acid | N | 3.8 | −16.24 ± 1.47 | 50.98 ± 4.12 |
| 100 mM Citric Acid | Y | — | 0 | <3 |
| 100 mM Citric Acid | N | 3.4 | −11.99 ± 0.67 | 25.17 ± 1.01 |

Example 9

This example illustrates the changes in physical properties of putty materials due to sterilization by exposure to g-radiation.

Samples using 20 mM, 50 mM and 100 mM ascorbic acid solutions were prepared using the procedure of Example 5 and irradiated with 1.0 MRad of g-radiation by Sterigenics (Charlotte, N.C.). A comparative distance to peak force and peak force are shown on Table 10.

TABLE 10

Effect of g-radiation

| Acid | Sterilized? | pH | Distance (mm) | Peak Force (g) |
|---|---|---|---|---|
| 20 mM Ascorbic Acid | Y | 5.2 | 0 | <3 |
| 20 mM Ascorbic Acid | N | 5.0 | −2.94 ± 1.22 | 5.83 ± 1.2 |
| 50 mM Ascorbic Acid | Y | 4.6 | −6.53 ± 0.71 | 27.52 ± 3.03 |
| 50 mM Ascorbic Acid | N | 4.4 | −7.48 ± 1.05 | 38.81 ± 5.80 |
| 100 mM Ascorbic Acid | Y | 4.1 | −9.02 ± 0.16 | 18.80 ± 1.70 |
| 100 mM Ascorbic Acid | N | 4.1 | −11.79 ± 0.26 | 38.92 ± 1.13 |

Samples prepared with 50 mM or 100 mM ascorbic acid retained its putty texture even after being exposed to g-radiation.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. An osteogenic composition comprising:
   collagen;
   an osteoinductive material comprising an osteoinductive protein or protein mixture selected from the group consisting of bone growth protein, BMP 1, BMP-2, BMP-3, BMP-4, BMP-5, BMP-6, BMP-7, BMP-8, BMP-9, BMP-10, BMP-11, BMP-11, BMP-12, BMP-—and OP-1;
   and an acid effective to provide a pH of between about 3 and about 6;
   wherein the osteogenic composition comprises between about 0.05 mmol of said acid per 100 mg of said collagen to about 2.3 mmol of said acid per 100 mg of said collagen.

2. The osteogenic composition of claim 1, wherein said collagen is selected from the group consisting of fibrillar collagen, atelopeptide collagen, telopeptide collagen and tropocollagen.

3. The osteogenic composition of claim 2, wherein said collagen is bovine tendon Type I collagen.

4. The osteogenic composition of claim 1, wherein said acid is selected from the group consisting of ascorbic acid, acetic acid, acetyl salicylic acid, benzoic acid, citric acid, glutamic acid, glycolic acid, lactic acid, malic acid, salicylic acid, and hydrochloric acid.

5. The osteogenic composition of claim 4, wherein said acid is ascorbic acid.

6. The osteogenic composition of claim 5, wherein the osteogenic composition comprises between about 0.1 mmol of said ascorbic acid per 100 mg of said collagen to about 1.5 mmol of said ascorbic acid per 100 mg of said collagen.

7. The osteogenic composition of claim 1, wherein said osteoinductive material is selected from the group consisting of bone growth protein, BMP 1–13, and OP1.

8. The osteogenic composition of claim 7, wherein said osteoinductive factor is bone growth protein.

9. The osteogenic composition of claim 1, wherein the osteogenic composition is aseptic.

10. The osteogenic composition of claim 9, wherein the osteogenic composition is produced by sterilization with ethylene oxide.

11. The osteogenic composition of claim 9, wherein the osteogenic composition is produced by sterilization by an exposure to g-radiation.

12. The osteogenic composition of claim 1, wherein the osteogenic composition is dry.

13. The osteogenic composition of claim 1, wherein the osteogenic composition is a gel.

14. The osteogenic composition of claim 1, further comprising water.

15. The osteogenic composition of claim 1, further comprising a demineralized bone material.

16. A kit comprising the osteoinductive composition of claim 1, a demineralized bone material and a container for mixing the osteoinductive composition and the demineralized bone material.

17. An osteogenic composition comprising:
   bovine tendon Type I collagen;
   ascorbic acid;
   water;
   bone growth protein; and
   a demineralized bone material.

18. The osteogenic composition of claim 17, wherein the osteogenic composition comprises from about 0.05 mmol of said ascorbic acid per 100 mg of said collagen to about 2.30 mmol of said ascorbic acid per 100 mg of said collagen.

19. The osteogenic composition of claim 17, wherein the pH of the osteogenic composition is between about 3.0 to about 6.0.

20. The osteogenic composition of claim 17, wherein the osteogenic composition comprises from about 1.0% by weight to about 10.0% by weight collagen.

21. The osteogenic composition of claim 17, wherein the osteogenic composition comprises from about 0.1% by weight to about 10.0% by weight bone growth protein.

22. The osteogenic composition of claim 17, wherein the osteogenic composition comprises from about 80.0% by weight to about 98.9% by weight demineralized bone material.

23. The osteogenic composition of claim 17, wherein the peak resistance force of the composition having a trapozoidal shape measuring 53 mm (l)×4 mm (h)×4 mm (w) at one end and 2.5 mm (w) at another end is at least about 10 g.

24. The osteogenic composition of claim 17, wherein the extensibility of the composition having a trapezoidal shape measuring 53 mm (l)×4 mm (h)×4 mm (w) at one end and 2.5 mm (w) at another end is from about 2 mm to about 25 mm.

25. A composition produced from a process comprising the steps of:

admixing collagen, an acid, and water to form a gel; and adding a demineralized bone material to said gel to produce an osteogenic putty;

wherein the osteogenic putty has a pH of about 6.0 or less.

26. The composition produced from the process of claim 25, wherein said collagen is selected from the group consisting of fibrillar collagen, atelopeptide collagen, telopeptide collagen and tropocollagen.

27. The composition produced from the process of claim 26, wherein said collagen is bovine tendon Type I collagen.

28. The composition produced from the process of claim 25, wherein said acid is selected from the group consisting of ascorbic acid, acetic acid, acetyl salicylic acid, benzoic acid, citric acid, glutamic acid, glycolic acid, lactic acid, malic acid, salicylic acid, and hydrochloric acid.

29. The composition produced from the process of claim 28, wherein said acid is ascorbic acid.

30. The composition produced from the process of claim 25, wherein said process further comprises the step of sterilizing said gel before the step of adding said demineralized bone material.

31. The composition produced from the process of claim 30, wherein said step of sterilization comprises exposing said gel to g-radiation.

32. The composition produced from the process of claim 25, wherein said process further comprises the step of lyophilizing said gel before the step of adding said demineralized bone material.

33. The composition produced from the process of claim 32, wherein said process further comprises the step of sterilizing said lyophilized gel by contacting with ethylene oxide.

34. The composition produced from the process of claim 25, wherein said step of adding said demineralized bone material further comprises adding water.

35. The composition produced from the process of claim 25, wherein said step of admixing further comprises admixing an osteoinductive material.

36. The composition produced from the process of claim 35, wherein said osteoinductive material is selected from the group consisting of bone growth protein, BMP 1–13, and OP1.

37. The composition produced from the process of claim 36, wherein said osteoinductive material is bone growth protein.

* * * * *